(12) United States Patent
Lang (10) Patent No.: US 10,039,460 B2
(45) Date of Patent: Aug. 7, 2018

(54) NEURAL ACTIVITY RECORDING APPARATUS AND METHOD OF USING SAME

(71) Applicant: MiSleeping, Inc., Carmel, IN (US)

(72) Inventor: Todd J. Lang, Carmel, IN (US)

(73) Assignee: MiSleeping, Inc., Carmel, IN (US)

( * ) Notice: Subject to any disclaimer, the term of this patent is extended or adjusted under 35 U.S.C. 154(b) by 477 days.

(21) Appl. No.: 13/746,335

(22) Filed: Jan. 22, 2013

(65) Prior Publication Data

US 2014/0206975 A1  Jul. 24, 2014

(51) Int. Cl.
*A61B 5/0476* (2006.01)
*A61B 5/04* (2006.01)
*A61B 5/0478* (2006.01)

(52) U.S. Cl.
CPC ........ *A61B 5/04001* (2013.01); *A61B 5/0478* (2013.01)

(58) Field of Classification Search
CPC ... A61B 5/0476; A61B 5/0006; A61B 5/6814; A61B 5/0412; A61B 5/7225
USPC ............... 600/372–373, 382–383, 386–393, 600/544–545
See application file for complete search history.

(56) References Cited

U.S. PATENT DOCUMENTS

| | | | |
|---|---|---|---|
| 4,776,345 A | 10/1988 | Cohen et al. | |
| 4,836,219 A | 6/1989 | Hobson et al. | |
| 5,101,831 A | 4/1992 | Koyama et al. | |
| 5,280,791 A | 1/1994 | Lavie | |
| 5,479,934 A | 1/1996 | Imran | |
| 5,924,979 A | 7/1999 | Swedlow et al. | |
| 5,999,846 A | 12/1999 | Pardey et al. | |
| 6,381,481 B1 | 4/2002 | Levendowski et al. | |
| 6,811,538 B2 | 11/2004 | Westbrook et al. | |
| 7,297,119 B2 | 11/2007 | Westbrook et al. | |
| 7,593,767 B1 | 9/2009 | Modarres | |
| 7,654,948 B2 | 2/2010 | Kaplan et al. | |
| 7,711,506 B2 | 5/2010 | Burdett et al. | |
| 7,774,052 B2 | 8/2010 | Burton et al. | |
| 7,894,890 B2 | 2/2011 | Sun et al. | |
| 8,073,534 B2 | 12/2011 | Low | |

(Continued)

FOREIGN PATENT DOCUMENTS

| | | |
|---|---|---|
| CN | 200987667 | 12/2007 |
| WO | WO 2010042750 | 4/2010 |

OTHER PUBLICATIONS

Chaparala et al., A Novel Neural Network Classifier for Brain Computer Interface, Computer Engineering and Intelligent Systems, vol. 3, No. 3, 2012, 9 pages.

(Continued)

*Primary Examiner* — Joseph Stoklosa
*Assistant Examiner* — Brian M Antiskay
(74) *Attorney, Agent, or Firm* — Faegre Baker Daniels LLP (57) ABSTRACT

An apparatus to enable individuals to record neural activity. The apparatus is designed to be produced at a low cost and may be configured to be disposable or capable of a limited number of uses. The apparatus comprises electrodes, a flexible housing sealably enclosing an energy storage device and an integrated circuit having a memory, a processor, and on-board memory. The electrodes capture the neural activity signals. The integrated circuit samples the neural activity signals and stores corresponding data in memory.

22 Claims, 8 Drawing Sheets

(56) References Cited

U.S. PATENT DOCUMENTS

| | | | |
|---|---|---|---|
| 8,194,373 | B2 | 6/2012 | Padden |
| 8,232,813 | B2 | 7/2012 | Burdett et al. |
| 8,249,686 | B2 | 8/2012 | Libbus et al. |
| 2004/0015058 | A1 | 1/2004 | Besson et al. |
| 2005/0165323 | A1 | 7/2005 | Montgomery et al. |
| 2005/0223646 | A1 | 10/2005 | Kim |
| 2005/0280531 | A1* | 12/2005 | Fadem .................. A61B 5/0006 340/539.12 |
| 2006/0276702 | A1 | 12/2006 | McGinnis |
| 2006/0293608 | A1* | 12/2006 | Rothman ............. A61B 5/4812 600/545 |
| 2007/0016095 | A1 | 1/2007 | Low et al. |
| 2007/0129622 | A1 | 7/2007 | Bourget et al. |
| 2007/0244370 | A1 | 10/2007 | Kuo et al. |
| 2007/0249952 | A1* | 10/2007 | Rubin .................. A61B 5/0476 600/544 |
| 2007/0270678 | A1* | 11/2007 | Fadem .................. A61B 5/0006 600/372 |
| 2007/0287931 | A1 | 12/2007 | Dilorenzo |
| 2008/0027347 | A1 | 1/2008 | Harris et al. |
| 2008/0214946 | A1 | 9/2008 | Miller et al. |
| 2009/0024017 | A1* | 1/2009 | Ruffini .................. A61B 5/0408 600/395 |
| 2009/0062682 | A1 | 3/2009 | Bland et al. |
| 2009/0253996 | A1 | 10/2009 | Lee et al. |
| 2010/0099954 | A1 | 4/2010 | Dickinson et al. |
| 2010/0191074 | A1 | 7/2010 | Chou |
| 2010/0234697 | A1 | 9/2010 | Walter et al. |
| 2010/0299064 | A1 | 11/2010 | Hilbrandie et al. |
| 2011/0066054 | A1 | 3/2011 | Chen |
| 2011/0092834 | A1 | 4/2011 | Yazicioglu et al. |
| 2011/0224569 | A1* | 9/2011 | Isenhart ............... A61B 5/0476 600/544 |
| 2012/0029378 | A1 | 2/2012 | Low |
| 2012/0143020 | A1 | 6/2012 | Bordoley et al. |
| 2012/0277549 | A1 | 11/2012 | Libbus et al. |
| 2013/0317333 | A1* | 11/2013 | Yang ........................ A61B 5/00 600/372 |
| 2015/0133762 | A1* | 5/2015 | Hayakawa ........... A61B 5/0478 600/383 |

OTHER PUBLICATIONS

International Search Report and Written Opinion of the International Searching Authority in related application PCT/US2014/012461, dated Apr. 8, 2014, 8 pages.

DeLorme et al., EEGLAB: an open source toolbox for analysis of single-trial EEG dynamics including independent component analysis, Journal of Neuroscience Methods 134, 2004, pp. 9-21.

Lohr, High-Tech Alternatives to High Cost Care, The New York Times, May 23, 2010, 3 pgs.

Home Sleep Testing, sleepreviewmag.com, Sep. 2010, pp. 28-33.

Toumaz Sensium Life Platform, http://www.toumaz.com/page.php?page=sensium_life_platform, Nov. 28, 2012, 2 pgs.

Lee, Understanding the Terms and Definitions of LDO Voltage Regulators, Texas Instruments Application Report SLVA079, Oct. 1999, 13 pgs.

Toumaz Digital Plaster to Wirelessly Monitor Patient Vital Signs Hits Trials, http://singularityhub.com/2009/11/09/toumaz-digital-plaster-to-wirelessly-monitor-patien . . . , Nov. 28, 2012, 4 pgs.

Ultralow-Power 100-mA Low Dropout Linear Regulators, Production Data, Texas Instruments, SLVS203E, Jun. 1999, Revised May 2001, 24 pgs.

Chatila et al., Portable Brainwave Monitor, http://www.ti.com/corp/docs/landing/universityprogram/09_winners/U_or_AZ_Chatila.pdf, accessed May 20, 2011, 51 pgs.

Chi et al., Wireless non-contact Cardiac and Neural Monitoring, Wireless Health, (Online), 2010, 9 pgs.

Dijk et al., Portable Sleep Monitoring System (Online), 2003, pp. 249-251.

Jun et al., A Wirless EEG Sensors System for Computer Assisted Detection of Alpha Wave in Sleep, $27^{th}$ Annual International Conference of the Engineering in Medicine and Biology Society (Online), 2005, pp. 5351-5353.

Zmachine® 510 (K) Summary, http://www.accessdata.fda.gov/cdrh_docs/pdfl0/K101830.pdf (accessed May 20, 2011) 7 pgs.

SleepScout Portable Sleep Monitor, http://www.cadwell.com/products/psg/easyambulatorypsg/ambulatorybrochure.pdf (accessed May 20, 2011), 2 pgs.

Nihon Kohden—WEE-1000. http://www.nihonkohden.com/products/type/eeg/wee1000.html (accessed May 20, 2011), 2 pgs. pgs.

"A Designer's Guide to Instrumentation Amplifiers," $3^{rd}$ Edition, Charles Kitchin and Lew Counts, copyright 2006 by Analog Devices, Inc., available for download at http://www.analog.com/static/imported-files/design_handbooks/58127566674312778737Complete_In_Amp; 130 pages.

International Preliminary Report on Patentability issued by the European Patent Office, dated Jul. 28, 2015, in corresponding International Patent Application No. PCT/US2014/012461, 7 pages.

* cited by examiner

NEURAL ACTIVITY RECORDING APPARATUS AND METHOD OF USING SAME

CROSS REFERENCE TO RELATED APPLICATION

None.

FIELD OF THE DISCLOSURE

The disclosure relates generally to an apparatus for recording neural activity. More particularly, the disclosure relates to a low power disposable or limited use apparatus for recording neural activity, a method of using such an apparatus, and a system for recording neural activity with said apparatus.

BACKGROUND

An electroencephalograph produces an encephalogram (EEG) to represent graphically brain waves representing electrical activity in the brain. The EEG can be used to diagnose neurological disorders. The electroencephalograph measures neural activity signals using a plurality of electrodes adhered to the scalp of the patient. Differences in electric potential between different parts of the brain are measured with multiple galvanometers and printed simultaneously as waveform tracings that have standard configurations in the normal brain. Variations from standard waveforms may be indicative of a brain disorder. Neural activity signals can also be captured, processed and analyzed to determine how well a patient sleeps.

Digital signal processing techniques may be applied to detect non-standard neural waveforms and sleep modes. For example, event related potentials, e.g. amplitude and peak latency measures, have been compared across EEG trials representing brain responses to sensory stimulations to map the event related potentials and the sensory events. Other digital signal processing techniques, the fundamentals of which were developed in the fields of electrical engineering and information theory, include time/frequency analysis and independent component analysis. More complex electroencephalograph capabilities are required to provide more complex analysis. Equipment and analysis costs may be proportional to the complexity of the systems required to perform the analysis.

SUMMARY

An apparatus to enable individuals to record neural activity. The apparatus is designed to be produced at a low cost. The apparatus may be configured to be disposable or capable of a limited number of uses. The apparatus comprises electrodes, a flexible housing enclosing an integrated circuit having a memory, and an energy storage device. The electrodes capture the neural activity signals. The integrated circuit samples the neural activity signals and stores corresponding data in memory. The neural activity data may be transferred to a processing or recording device for analysis.

In one embodiment of a neural activity recording apparatus, the apparatus comprises at least two electrodes configured to establish an electrical path through a patient's skin and to acquire a neural activity signal; an amplifier circuit configured to receive the neural activity signal and to output an amplified neural activity signal; and an integrated circuit (IC) including a processor, an analog-to-digital converter (ADC), an IC memory, and an efficient line frequency filter algorithm embedded therein, the ADC configured to receive and digitize the amplified neural activity signal to produce a sample stream, the efficient line frequency filter algorithm configured to cancel a substantial portion of a line frequency noise embedded in the sample stream to generate a neural activity data. The apparatus further comprises an energy storage device configured to energize the IC and the amplifier circuit; and a housing enclosing the IC and the energy storage device and supporting the electrodes.

In one variation thereof, the apparatus further includes a removable memory configured to store the neural activity data. In one example, removal of the removable memory requires destruction of the housing.

In another variation, the apparatus further comprises a wireless transceiver configured to output the neural activity data.

In another variation, the ADC is configured to sample the amplified neural activity signal at an integer multiple of a power line frequency, the multiple being greater than 1.

In another variation, the efficient line frequency filter algorithm is configured to divide the sample stream into at least two sub-streams, to compute moving averages for each sub-stream, and to compute the neural activity data based on the moving averages of the at least two sub-streams.

In another variation, the IC further includes an digital-to-analog converter (DAC) configured to generate a common mode noise cancellation signal, wherein the common mode noise cancellation signal is provided to the instrumentation amplifier to cancel a common mode noise signal.

In another variation, the apparatus further comprises an indicator device configured to provide sleep quality feedback. In one example, the sleep quality feedback is provided continuously. In another example, the apparatus further comprises a transducer outputting transducer signals, and the IC correlates the transducer signals with the neural activity data to determine the sleep quality feedback. Exemplary transducers include motion and air flow transducers.

In one embodiment of a neural activity recording apparatus, the apparatus comprises at least two electrodes configured to establish an electrical path through a patient's skin and to acquire a neural activity signal; an amplifier circuit configured to receive the neural activity signal and to output an amplified neural activity signal; and an integrated circuit including a processor, an analog-to-digital converter, an IC memory, and an algorithm embedded therein configured to generate a neural activity data representative of sleep/wake patterns. The apparatus further comprises an energy storage device configured to energize the IC and the amplifier circuit; a removable memory configured to store the neural activity data; and a housing enclosing the IC, the removable memory and the energy storage device and supporting the electrodes, wherein the housing is altered by a user to remove the removable memory. In one example thereof, the apparatus further comprises a DAC configured to generate a common-mode noise reducing signal.

BRIEF DESCRIPTION OF THE DRAWINGS

The above-mentioned and other disclosed features, and the manner of attaining them, will become more apparent and will be better understood by reference to the following description of disclosed embodiments taken in conjunction with the accompanying drawings, wherein.

Corresponding reference characters indicate corresponding parts throughout the several views. Although the drawings represent embodiments of various features and components according to the present invention, the drawings are not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION

The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates.

A neural activity recording apparatus to enable individuals to record neural activity is disclosed herein. The apparatus is designed to be produced at a low cost and may be configured to be disposable or capable of a limited number of uses. The apparatus comprises electrodes, a flexible housing sealably enclosing an integrated circuit having a memory, and an energy storage device. The electrodes capture the neural activity signals. The neural activity recording apparatus further comprises a processing unit and a sampling algorithm configured to cause the processing unit to sample the neural activity signals and store neural activity data in memory. The neural activity data is transferred to a processing device for analysis.

In one variation of the present embodiment, the apparatus is sized to be attached to the forehead of a person with an adhesive layer and to record neural activity for a time period limited by the energy stored in the energy storage device. In one example, the apparatus is activated by removing an energy release strip. Upon removal of the strip, energy flows to the integrated circuit and neural signal sampling and recording automatically begins.

In another variation, two conductive skin electrodes are integrated into the housing and provide a conductive path for the neural activity signals from the skin to the inputs of an instrumentation amplifier, where the difference of the signals is amplified while common mode noise signals are suppressed. The instrumentation amplifier comprises common mode cancellation logic configured to remove or neutralize a direct current (DC) or alternating current (AC) common mode signal on the input signal which would cause saturation of the instrumentation amplifier. With microcontroller-based system-on-chip integrated circuits, dramatic changes to internal functional blocks can be made by changing a small number of external components or by programming dedicated embedded registers. Thus, a signal's path can be designed without costly hardware redesign, further reducing design and manufacturing costs and making a disposable diagnostic device practical. In one example, the instrumentation amplifier comprises an active filter implemented by adding passive electronic components to the feedback circuits of the instrumentation amplifier. The active filter may also perform an anti-aliasing function to prevent a frequency shift in the ADC. In another example, a digital-to-analgo converter DAC may be used to generate an out-of-phase common mode feedback signal to cancel the common mode signal. A DAC present in the system-on-chip integrated circuit may be used, thus preserving the system's simplicity.

Instrumentation amplifiers are well known and may be configured, for example, with two or three operational amplifiers. Exemplary instrumentation amplifier circuits are described in "A Designer's Guide to Instrumentation Amplifiers," 3rd Edition, by Charles Kitchin and Lew Counts, copyright 2006 by Analog Devices, Inc., available for download at http://www.analog.com/static/imported-files/design_handbooks/5812756674312778737Complete_In_Amp.pdf, which is incorporated herein by reference. An exemplary three op-amp instrumentation amplifier is shown therein on page 2-2, showing two input voltage nodes $V_{IN1}$ and $V_{IN2}$ and a reference node. The electrodes are connected to $V_{IN1}$ and $V_{IN2}$ and the common mode feedback signal output by the DAC is provided to the reference node. An exemplary two op-amp instrumentation amplifier is shown therein on page 2-5, also showing two input voltage nodes $V_{IN1}$ and $V_{IN2}$ and a reference node. Instrumentation amplifiers can be implemented using operational amplifiers built-in system-on-chip integrated circuits such as the MSP430 integrated circuit IC discussed below, which is distributed by Texas Instruments, Inc. The MSP430 IC also includes a 16 bit sigma-delta ADC, which offers high noise rejection and good cancellation of the input noise at a frequency coinciding with the ADC sampling frequency. This choice allows significant simplification of the analog circuit and of subsequent digital filtering.

In one embodiment, the neural activity recording apparatus is configured to record neural activity signals suitable to diagnose sleep/wake patterns. In the present embodiment, a signal in a certain bandwidth is generated by the patient's body and conducted through the electrodes. neural activity signals in a bandwidth limited to 30 Hz have been shown as adequate for recording and analyzing sleep/wake patterns. An effective cancellation of the power line frequency noise can be achieved by selecting the data sampling frequency to be a frequency equal to the line frequency times an integer value greater than zero, which will be referred to herein as a multiple of the line frequency even though the multiple can equal 1. For example, with power lines in North America having a line frequency of 60 Hz, adequate bandwidth can be established even when sampling at 60 Hz (multiple=1). Sampling frequencies where N is greater than 1 may achieve broader bandwidth and more accurate recording, especially when an efficient power line frequency noise removal filter is used. Similarly, a bandwidth of at least 25 Hz can be achieved if the line frequency is 50 Hz. An exemplary efficient power line frequency noise removal filter is described below.

Figure 1:
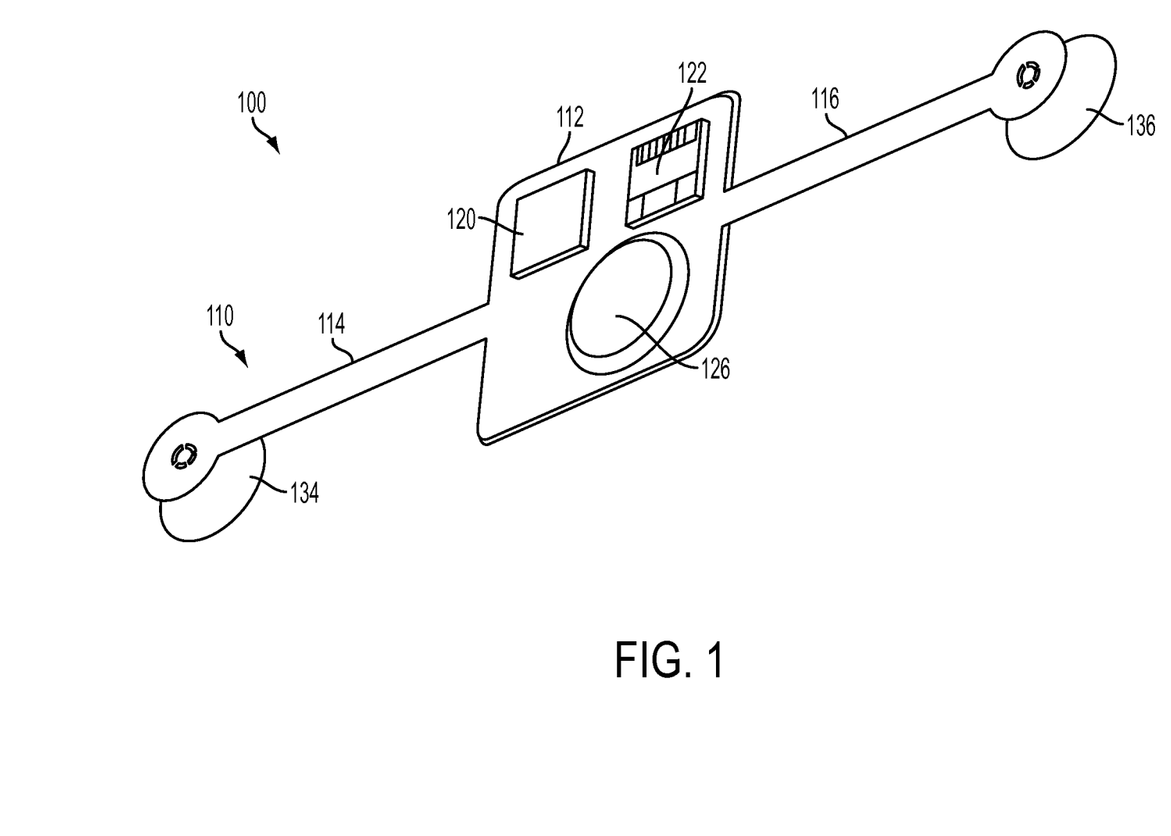
FIG. 1 is a perspective view of an embodiment of a neural activity recording apparatus.

In one example, the neural activity recording apparatus comprises an integrated circuit comprising a plurality of operational amplifiers, the ADC, the DAC, a processor and memory, and is suitable to form the instrumentation amplifier, to sample the neural activity signal, and to store the neural activity data in memory reciding in the IC or in a removable memory connected to it as shown on FIG. 1. A coin cell or even smaller battery may be used to power the neural activity recording apparatus circuits due to their extreme simplicity and low power consumption. If the apparatus is configured as a single use device, no charging or power monitoring circuits are necessary. With removable memory, such as a microSD card, a direct interface to an external reader is not necessary, so isolation circuits may be omitted.

In another example, the neural activity recording apparatus comprises an integrated circuit comprising a plurality of operational amplifiers, the ADC, the DAC, a processor, memory and a signal interface, and is suitable to form the instrumentation amplifier, to sample the neural activity signal, and to store the neural activity data in memory. The signal interface is provided to establish a communication path with an external device to which the neural activity data may be downloaded. The signal interface only becomes available after the housing of the neural activity recording apparatus is unsealed after use. Thus, isolation circuits may be omitted.

In a further example, the integrated circuit comprises a plurality of operational amplifiers, the ADC, the DAC, a processor, memory and wireless transmitter, and is suitable to form the instrumentation amplifier, to sample the neural activity signal, and to store the neural activity data in memory. The wireless transmitter is provided to establish a communication path with an external device to which the neural activity data may be wirelessly transmitted. A switch or sensor may be provided to initiate downloading of the stored neural activity data to the external device.

In another embodiment, the neural activity recording apparatus comprises an efficient power line frequency noise removal filter. In one example, the filter comprises a multiple stream line frequency notch filter algorithm stored in memory and configured to cause the ADC to sample the neural activity signal, or a signal corresponding to it, at a multiple of the line frequency. The algorithm then causes the samples to be divided into multiple data streams, the number of streams corresponding to the line frequency multiple. As a consequence, samples in each stream will fall at or close to the same phase of the line frequency. Averages are then computed for each stream and subtracted from corresponding samples. The running average in each stream will represent an approximation of the portion of the amplitude of the input signal due to residual line noise. Subtraction thus cancels the approximated line noise. The simplicity and iterative character of the algorithm significantly reduces the processing load compared with typical digital filters and effectively provides a very sharp notch filter without a hardware digital-signal-processing circuit.

In one variation of the present embodiment, moving averages $V_j$ of each stream are computed and indexed to a sample $S_j$. Then, averages $B_j$ are calculated for each sample out of all the moving averages corresponding to several adjacent samples (such that averages from each steam are included). Finally, a subtraction is performed to subtract from each sample S, the difference between the corresponding moving average from the individual stream V and the average of adjacent averages B, so that $S'_j = S_j - (V_j - B_j)$. The foregoing algorithm may be implemented with a stack, a matrix or a FIFO buffer, for example.

In a further embodiment, the neural activity recording apparatus comprises an indicator device. Exemplary indicator devices include logical indicators, e.g. lights, and displays configured to output information, e.g. alphanumeric or graphical displays. In one example, the integrated circuit comprises circuitry for driving the indicator device. The indicator device may be configured to provide functional indications. Exemplary functional indications include power, memory and energy availability, processing errors, and alarms triggered from the evaluation of the neural activity data.

In a yet further embodiment, the neural activity recording apparatus is configured to provide sleep quality feedback. In one example, the apparatus indicates sleep quality feedback with the indicator device. In one example, the sleep quality feedback is provided continuously. For example, the indicator may be caused to flash at predetermined rates indicative of sleep quality or the alphanumeric display may provide a sleep feedback number representing sleep quality.

In another embodiment, the neural activity recording apparatus further comprises a sleep quality transducer. The apparatus correlates transducer signals with the neural activity data to enable determination of sleep quality. In one example, the apparatus comprises a sleep quality algorithm configured to determine the sleep quality feedback and to provide an indication thereof with the indicator device. In another example, the quality feedback is determined by the external processing device after the neural activity data has been transferred. Exemplary sensors include motion and air flow transducers, snoring microphones, body position sensors, electromiography (EMG) and electrooculography (EOG) electrodes, accelerometers and light sensors. In one example, the apparatus determines low sleep quality feedback when it detects light changes or frequent body position changes. In another example, the apparatus distinguishes Rapid Eye Movement (REM) sleep stages frequently associated with quality sleep based on lack of muscle tone, characteristic EOG patterns and documented patterns in neural activity. The additional one or more transducers may be connected to existing channels in the system-on-chip IC described above. An exemplary indicator, denoted as light emitting diode indicator 1030, and an exemplary transducer, denoted as sleep quality transducer 1040, are described in connection with FIG. 10.

The following examples are operable, alone or in combination, with any of the foregoing embodiments and variations. In one example, the neural activity data is transmitted wirelessly to the processing and/or recording device. In another example, the neural activity data is transmitted to the processing device by removing a removable memory from a memory socket and reading the removable memory by the processing device. In a variation thereof, the removable memory is removed after permanently damaging the sealing housing. In a further example, a signal amplifier is positioned near an electrode to reduce noise while sensing the neural signals thereby increasing the signal-to-noise ratio of the amplifier's output signal. Reduced noise reduces the necessity to include additional filtering components and other components necessary to generate a usable signal from a low amplitude noisy signal. In a yet further example, the electronic components are not electrically isolated. Non-isolation contributes to the reduced component count and reduces the size and power demand of the apparatus.

Figure 2:
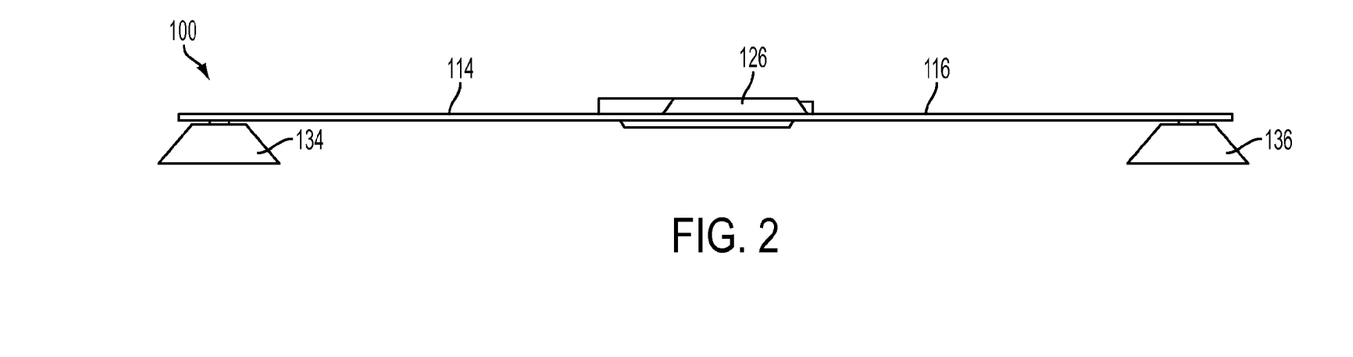
FIGS. 2 and 3 are elevation and plan views of the neural activity recording apparatus of FIG. 1.
Figure 3:
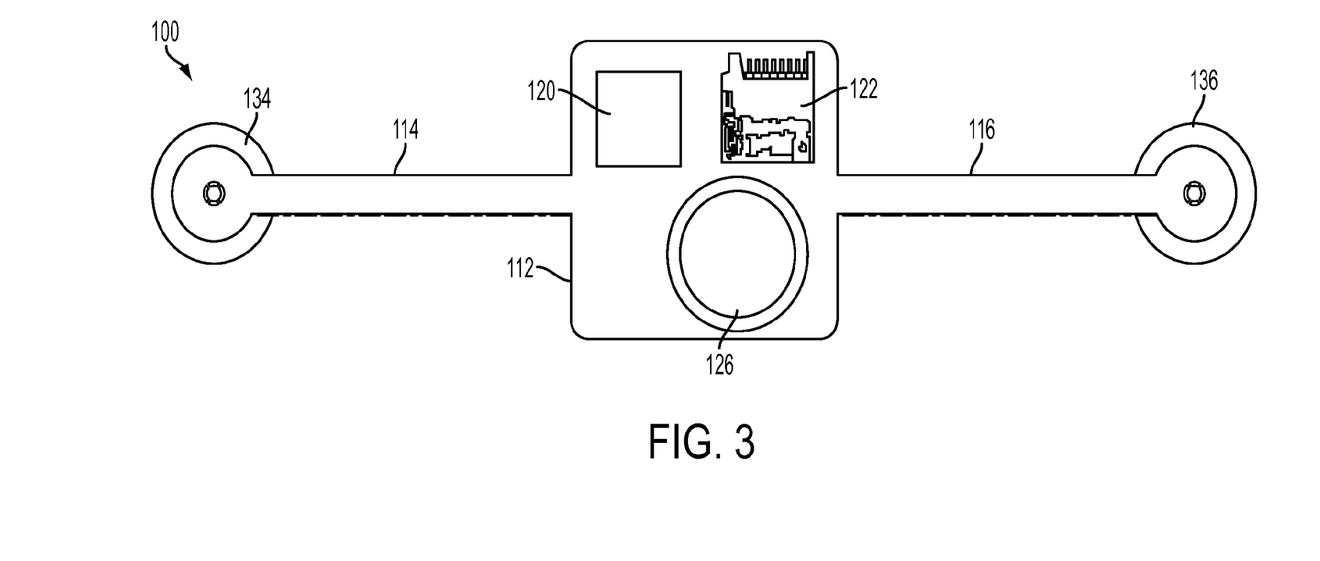

For the purposes of promoting an understanding of the principles of the invention, reference will now be made to the embodiments illustrated in the drawings, which are described below. FIG. 1 is a perspective view of an embodiment of a neural activity recording apparatus denoted by the numeral 100. FIGS. 2 and 3 are elevation and plan views of neural activity recording apparatus 100. Neural activity recording apparatus 100 comprises a housing (housing 400, shown in FIGS. 4 and 5) sealably enclosing a flexible substrate 110 including a body 112 and arms 114, 116. Flexible substrate 110 supports an integrated circuit 120, a memory socket 122, an energy storage device 126 and electrodes 134, 136. Integrated circuit 120 receives neural signals acquired by electrodes 134, 136 and stores neural activity data in a memory device (not shown) inserted in memory socket 122. Energy storage device 126 provides energy to integrated circuit 120 and memory socket 122 to enable their operation.

Figure 4:
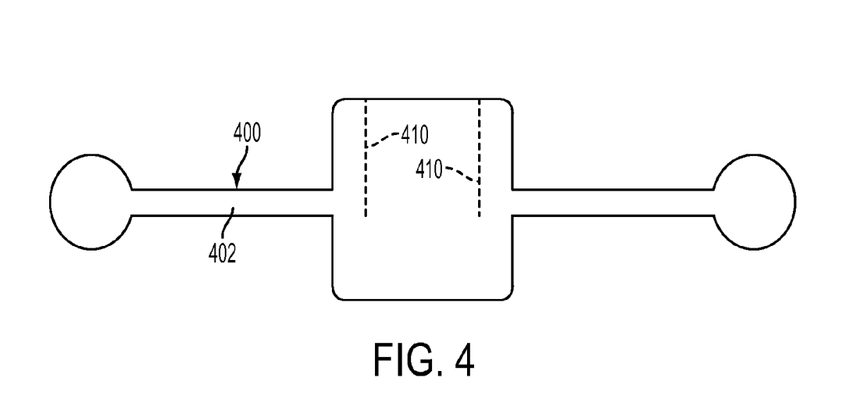
FIGS. 4 and 5 depict opposite views of an embodiment of a housing configured to sealably enclose the neural activity recording apparatus of FIG. 1.
Figure 5:
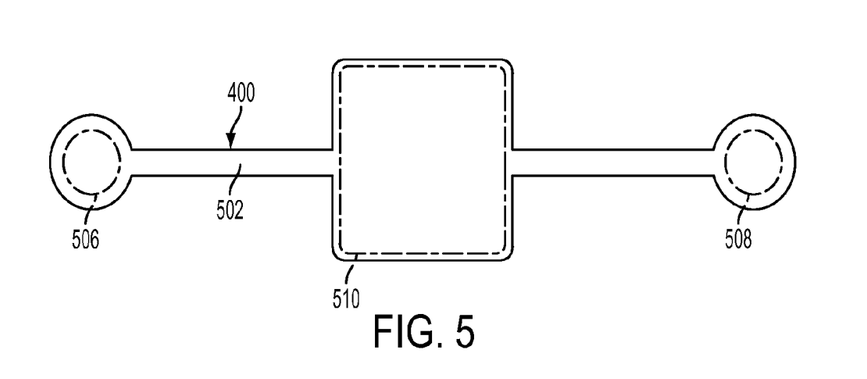

FIGS. 4 and 5 depict opposite views of an embodiment of a housing, denoted by numeral 400, configured to sealably enclose neural activity recording apparatus 100. Referring to FIG. 4, housing 400 has a shape that is similar to the shape of neural activity recording apparatus 100. In the portion of housing 400 corresponding to body 112, a pair of tear-marks 410 are provided to enable a user to tear housing 400 to remove the removable memory. Referring to FIG. 5, an adhesive material is disposed upon areas 506, 508 and 510 to enable a user to attach neural activity recording apparatus 100 on a person's skin. The side shown in FIG. 4, denoted by numeral 402, may be referred to as the free side. The side shown in FIG. 5, denoted by numeral 502, may be referred to as the attachment side. The terms "attachment" and "free" will be used in the same manner in connection with additional embodiments of housings or neural activity recording apparatus.

Figure 6:
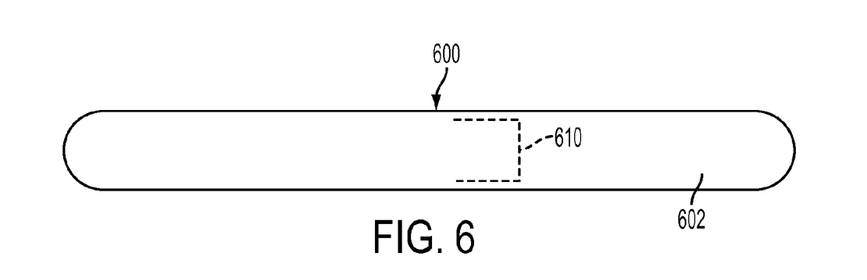
FIG. 6 depicts another embodiment of a housing configured to sealably enclose a neural activity recording apparatus.

FIG. 6 depicts a free side 602 of another embodiment of a housing, denoted by numeral 600, configured to enclose a neural activity recording apparatus (not shown). In one example, the neural activity recording apparatus positioned inside housing 600 includes a body and two arms, as discussed above. Optional tear-marks 610 are provided to enable a user to tear housing 600 to remove the removable memory. In a variation thereof configured to enclose a wireless neural activity recording apparatus, tear-marks 610 are omitted. In another example, the neural activity recording apparatus comprises an instrumental amplifier located near one electrode at one end of housing 600. Another electrode is located at the opposite end of housing 600, along a longitudinal direction. In a further example, the neural activity recording apparatus comprises an instrumental amplifier located near one electrode at one end of housing 600 and an amplifier near another electrode, which is located at the opposite end of housing 600, along a longitudinal direction. Two-amplifier configurations are described below with reference to FIGS. 9 and 10.

In a variation of the preceding embodiments, adhesive is omitted and, instead, the neural activity recording apparatus is supported by a wearable device worn by the patient. Exemplary wearable devices include hats, helmets and headbands. It should be understood that the term patient, as used herein, refers to the person whose neural activity is to be recorded with the neural activity recording apparatus.

Figure 7:
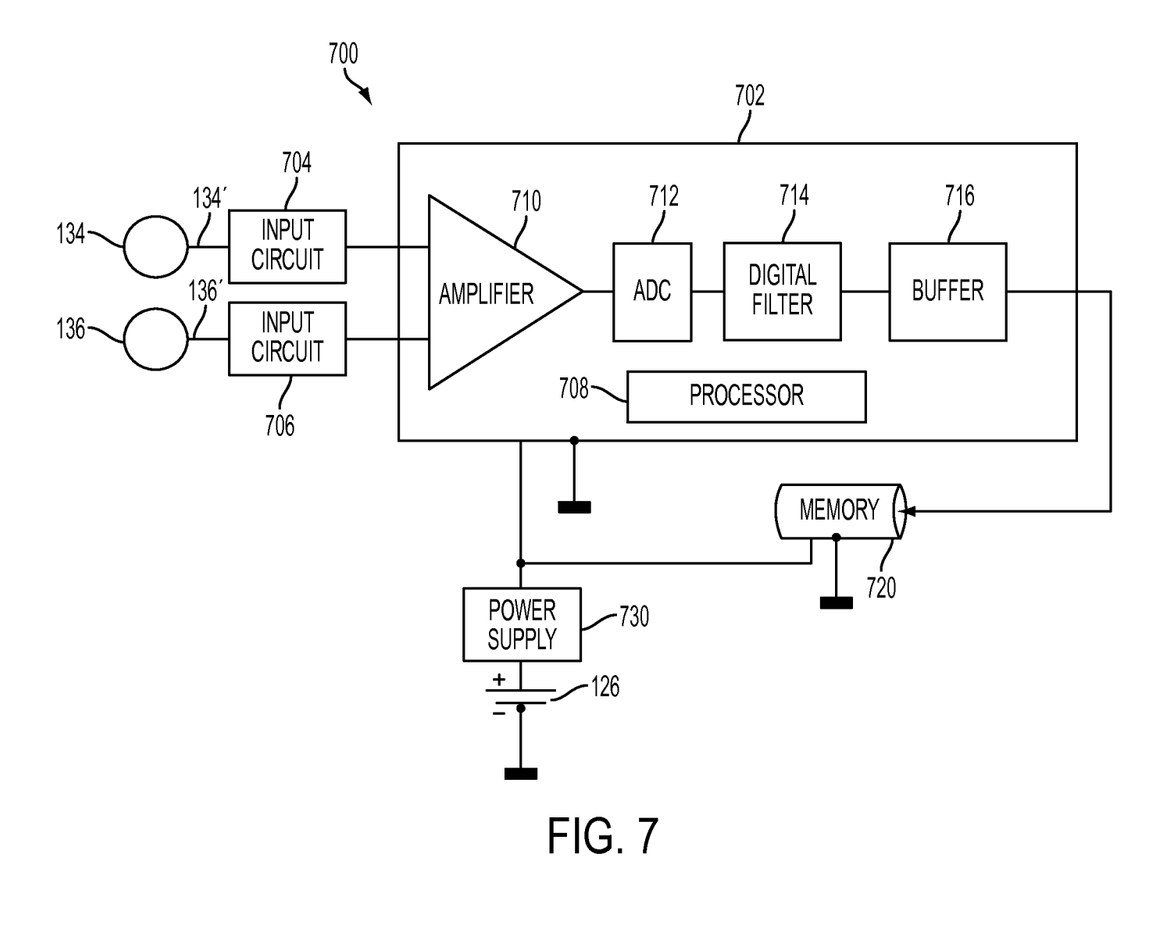
FIGS. 7 to 10 are block and schematic diagrams of additional embodiments of a neural activity recording apparatus.

FIG. 7 is a block diagram of another embodiment of a neural activity recording apparatus, denoted by numeral 700. Neural activity recording apparatus 700 comprises electrodes 134 and 136 coupled by conductors 134' and 136' to optional input circuits 704 and 706, which may provide analog filtering and stabilization of the neural signals. Input circuits 704 and 706 may comprise passive components for configuring the instrumentation amplifier, as described above. Neural activity recording apparatus 700 also comprises an integrated circuit 702, a memory 720 and a power supply 730. Power supply 730 receives power from energy storage device 126. Exemplary energy storage devices include batteries and capacitors. Power supply 730 may comprise a voltage or current regulator configured to supply a predetermined constant voltage or current level to integrated circuit 702 and memory 720, even as the charge level of energy storage device 126 decreases over time. Integrated circuit 702 is configured to perform a plurality of functions and comprises a processor 708. Integrated circuit 702 may also comprise a differential amplifier portion 710, an ADC portion 712, a digital filter logic 714 and a buffer portion 716. Furthermore, integrated circuit 702 may also comprise a DAC portion (not shown) configured to drive a common mode feedback signal to reduce or eliminate the DC voltage offset on the patient's body as described above in connection with the instrumentation amplifier. A common mode feedback signal 920 is shown on FIG. 9. Each portion may comprise hardware, software and a combination of hardware and software. It should be understood that integrated circuit 702 may comprise on-board memory having embedded therein algorithms to perform the functions. Further, it should be understood that integrated circuit 702 may comprise a sampling algorithm configured to control operation of ADC 712 and buffer 716, and that buffer 716 may represent an allocated memory portion of the on-board memory. Alternatively, hardware circuits may be provided to trigger the sampling rate of ADC 712. Further, digital filter logic 714 may comprise an algorithm configured to receive digital data from ADC portion 712 and to filter the digital data. Digital filtering may comprise, for example, computing an average, a moving average, maximum, minimum and range values, moving ranges, variances, trends and other statistical functions configured to represent patterns in the digital data. In one example, only statistical representations of the data are stored in memory to reduce the amount of memory required by the device. The data may also be processed to derive physiologically relevant information. In another example, only physiologically relevant data is stored in memory to reduce the amount of memory required by the device. The device may comprise physiologically relevant signature patterns stored in memory. The device may compare the physiologically relevant signature patterns with the data to identify physiologically relevant data. The physiologically relevant signature patterns may be stored in tables, as formulas or rules, and in any other known or later developed format.

Figure 8:
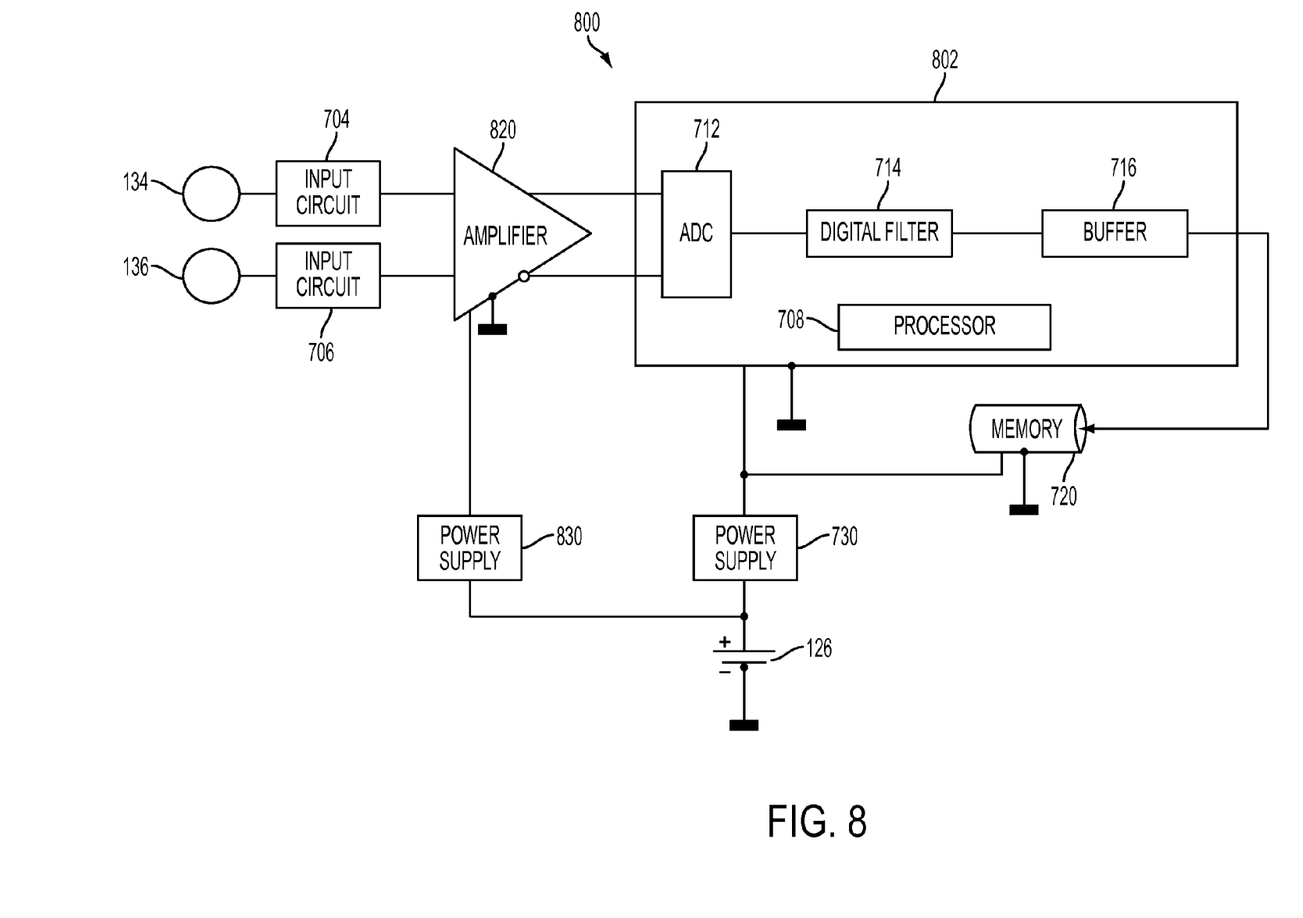

FIG. 8 is a block diagram of another embodiment of a neural activity recording apparatus, denoted by numeral 800. Neural activity recording apparatus 800 is similar to neural activity recording apparatus 700 except that amplifier portion 710 has been removed from integrated circuit 702 and an amplifier circuit 820 has been added externally of an integrated circuit 802. Further, an optional second power supply 830 is shown which can be added in case amplifier circuit 820 requires a different voltage level or to position power supply 830 near amplifier circuit 820, to reduce noise for example. As in neural activity recording apparatus 700, the differential neural signal is digitized and filtered before it is stored in memory 720. Sampling and filtering algorithms may be embedded in on-board memory to control ADC 712 and perform digital filtering.

In one variation of the embodiments disclosed in FIGS. 7 and 8, buffer portion 716 may comprise on-board memory having stored therein an output algorithm configured to periodically read the digital data, or filtered representations thereof, and output the data to memory 720. Buffer portion 716 may output data at a predetermined fixed rate or the rate may be determined based on the occurrence of predetermined events. In one example, a cyclic buffer is used to record signal data, statistical data or derived physiological relevant data both immediately preceding and immediately following an event of interest. Exemplary events of interest include an external event detected by a sensor or a transducer (such as a motion or airflow transducer) or a moment detection that is performed by a signal processing algorithm based on an neural activity signal level or data captured from a transducer.

Memory 720 comprises any computer-readable storage device suitable to store data. Exemplary memory includes flash memory, both removable and permanently attached. In a further variation, memory 720 is embedded in integrated circuit 702.

In a further variation, the neural activity recording apparatus includes a sampling algorithm configured to store the output of ADC portion 712 in memory 720 without further processing, e.g. without filtering or buffering.

Figure 9:
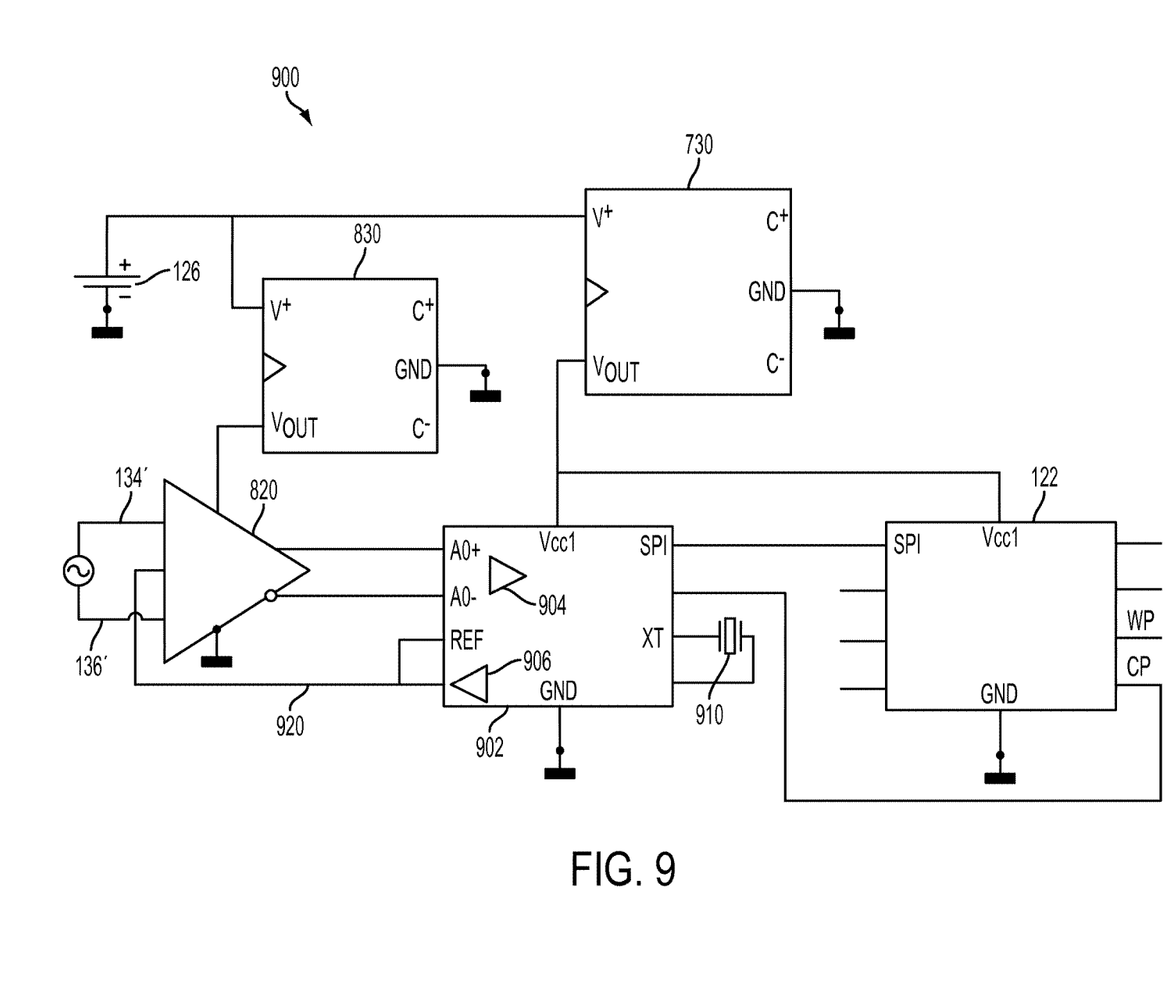

FIG. 9 is a circuit diagram of another embodiment of a neural activity recording apparatus, denoted by numeral 900. Neural activity recording apparatus 900 is similar to neural activity recording apparatus 800 and may be implemented as described above, including any of the variations thereof. An integrated circuit 902 is provided, which is similar to integrated circuit 802 and further comprises an instrumentation amplifier 904 and a DAC 906 in addition to the previously described components (not shown), such as processor 708 and ADC 712. Neural activity recording apparatus 900 includes a crystal oscillator 910 which determines the operating frequency of processor 708. A common mode reference signal is provided by DAC 906 via a conductor 920, to amplifier circuit 820. The reference signal may be generated by the sampling algorithm, which may be configured to determine the amplitude of the common mode signal and to cause DAC 906 to generate a common mode feedback signal to substantially negate the common mode signal. In one example of neural activity recording apparatus 900, the components described above comprise the following exemplary integrated circuits:

| COMPONENT | EXAMPLE |
| --- | --- |
| Power supply 730 | Texas Instruments ultra low power low dropout (LDO) linear regulator TPS76930 |
| Power supply 830 | Texas Instruments ultra low power LDO linear regulator TPS76933 |
| Amplifier circuit 820 | Texas Instruments very low power fully differential amplifier THS4524 |
| Integrated circuit 802 | Texas Instruments 16-bit ultra low power RISC microcontroller with flash memory, random access memory, five low power modes of operation (including active and standby), serial communication interface, digitally controlled oscillator, and sigma-delta ADC, MSP430f425A or MSP430F47197 (up to 7 channels) |

A low frequency (below 30 Hz) signal is generated by the patient's body and is transmitted through the electrodes to the instrumental amplifier and analog and digital circuits that capture the neural activity signals. In one example, amplifier 820 is be positioned within millimeters of an electrode in order to increase the level of integration and reduce noise generation while sensing the EEG signals. Due to the flexibility of arms 114, 116 amplifier 820 may be located directly above the selected electrode. The other electrode may be extended using a flexible circuit board or flexible conductors. In another example, amplifier 820 is located between a pair of electrodes. In a further example (not shown), amplifier 820 is positioned near one electrode at one end of the neural activity recording apparatus and IC 902 is be positioned near another electrode at the opposite end of the neural activity recording apparatus, thereby positioning both amplifiers near the electrodes to further reduce noise. Such a configuration may be housed in housing 600 or a similarly shaped housing. Actively driven shields may be employed with any of the foregoing embodiments and examples to further reduce the level of noise.

As described previously, in one embodiment the neural activity recording apparatus comprises an efficient line frequency digital filtering algorithm. In one example, the algorithm is configured to sample the neural activity signal at double the line frequency, where N=2 and j is a sample index. Thus, if the line frequency is 60 Hz, the sampling frequency is 120 Hz and the sample stream includes samples Sj. The data stream Sj is then sequentially divided into N streams. If N=2, odd samples go to the first stream and even samples go to the second stream. Averages are then computed for each stream. Each average may comprise a moving average of K samples. K is selected such that the variance of the line frequency during the time period represented by K samples is small relative to the average line frequency. With typical power line frequency fluctuations of 1 to 3 percent, a value of K=10 was empirically found to produce suitable results.

Consider i to be a running index in each of the N sub-streams. Each average is assigned to a variable so that if Si is an amplitude of a sample at index i in the sub-stream n (n is between 1 and N), then Vi is the average of the last K samples in that sub-stream preceding and including i. For each sample in the original stream Sj there is a corresponding moving average Vj.

Averages are then subtracted from corresponding samples. In general i(n) (an index within the sub-stream n) is related to j (the original index) as j=(i(n)−1)*(N)+n. For each sample Sj, calculate the average of all adjacent averages Vm, where m is from j to j+(N−1), and assign this average to a variable Bj. Then, replace Sj with Sj−(Vj−Bj). In one example, where the line frequency is 60 Hz, N=2 and K=10, and the sampling frequency is 120 Hz, averages are computed for each 10 subsequent points or over ⅙ of a second.

Figure 10:
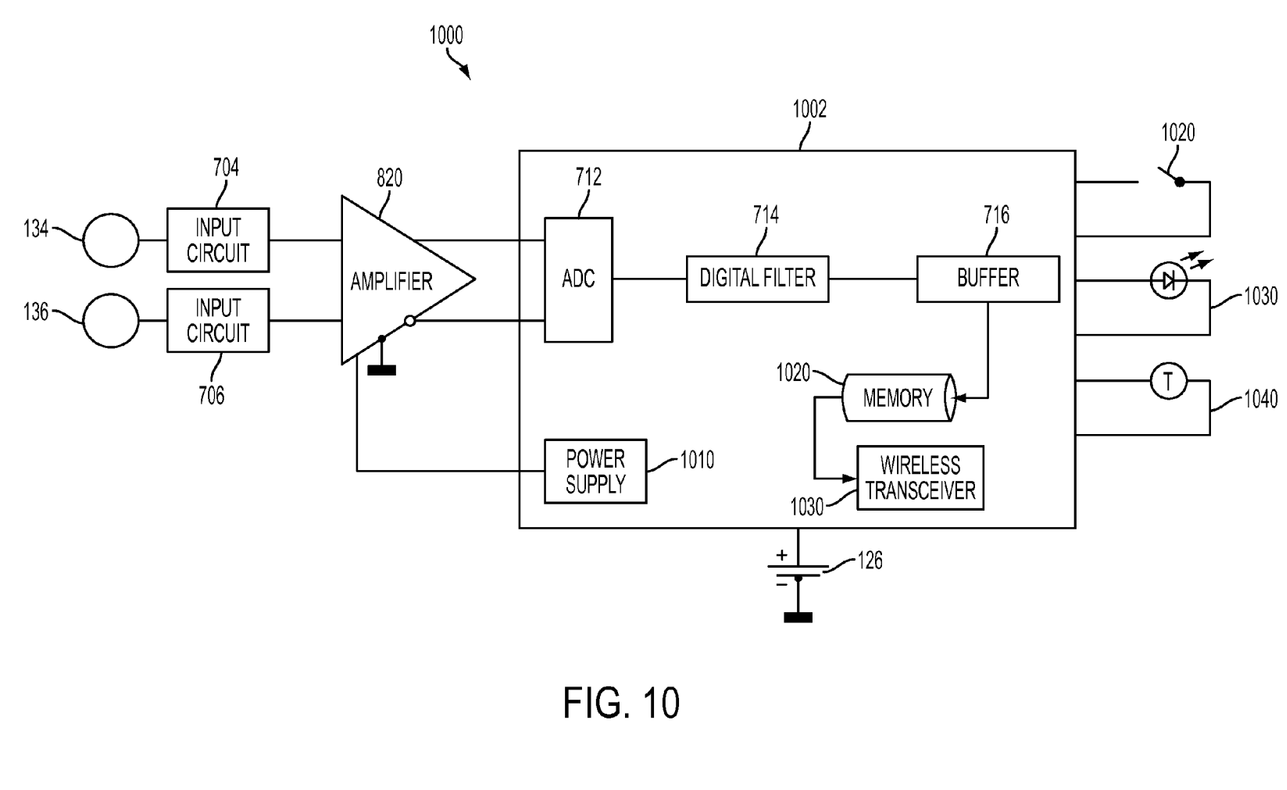

FIG. 10 is a circuit diagram of another embodiment of a neural activity recording apparatus, denoted by numeral 1000. Neural activity recording apparatus 1000 is similar to neural activity recording apparatus 900 except that it comprises an IC 1002 including a power supply portion 1010 configured to power amplifier circuit 820, on-board memory 1020, and a wireless transceiver 1030. Neural activity recording apparatus 1000 may be implemented including any suitable variation and example described above. An external memory socket and memory is not required. On-board memory 1020 may have embedded therein the sampling algorithm. In one example, digital filter logic 714 is also embedded in on-board memory 1020. In one example, buffer 716 comprises a portion of on-board memory 1020. After processing, the data is stored in memory 1020. The data is then transmitted wirelessly to a processing or recording device. Of course, additional processing may be performed before loaded data is transmitted. In a variation thereof, wireless transceiver 1030 is substituted by a data interface operable to transfer data to the processing or recording device. In a further variation thereof, input circuits 704 and 706 are omitted. In a further variation thereof, IC 1002 further includes an instrumental amplifier logic interposed between amplifier circuit 820 and ADC 712.

In further embodiments described below, the use of a switch, indicator and sleep quality transducer are described. An optional switch 1020, light emitting diode indicator 1030, and transducer 1040 are shown, which may be programmed to provide the optional functionality described below. One or more of switch 1020, light emitting diode indicator 1030, and transducer 1040 may also be incorporated with neural activity recording apparatus 700, 800 and 900.

Figure 11:
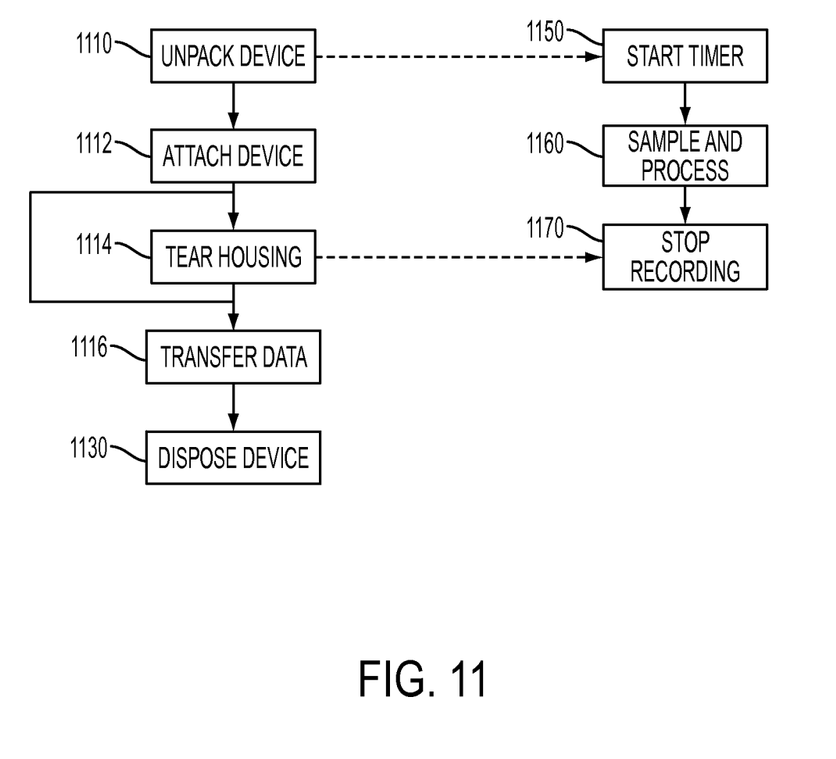
FIG. 11 is a flowchart depicting an embodiment of a method for recording neural activity.

FIG. 11 is a flowchart depicting an embodiment of a method for recording neural activity with a neural activity recording apparatus. At unpack apparatus 1110, an energy release strip contacting an energy storage device is displaced to enable power from the energy storage device to power the neural activity recording apparatus.

At attach apparatus 1112, the neural activity recording apparatus is attached to the patient's forehead. The apparatus may be attached with adhesive or with a wearable device, e.g. a strap or hat.

Optionally, at start timer 1150, a timer logic automatically beings to track the time the neural activity recording apparatus has been powered. The apparatus may be programmed to cease operating after a predetermined amount of powered time has passed.

At sample and process 1160, the neural activity recording apparatus samples signals provided by at least two electrodes at a line frequency integer multiple greater than zero. Upon attachment of the apparatus to the patient, the sampled data beings to represent neural activity signals. In one example, the apparatus obtains and stores statistical or physiological representations of the neural activity data. In a further example, the apparatus divides the sampled data into a number of processing streams equal to the value of a line frequency sampling multiple to filter line frequency related noise from the sampled data without a hardware digital signal processing circuit. In a yet further example, the apparatus evaluates a common mode signal level and generates a corresponding common mode feedback signal with a DAC to substantially negate the common mode signal. Processed data is then recorded.

At stop recording 1170, the neural activity recording apparatus stops recording data. The apparatus may stop recording data based on the occurrence of an event. Exemplary events include a determined value exceeding or being less than a corresponding predetermined threshold. Exemplary predetermined thresholds include powered time, energy storage level, absence of neural activity signals, absence of neural activity signals after a predetermined amount of data has been recorded, amount of recorded data, available memory, a transducer signal indicative of a patient's activity, physiological condition or position, and any other suitable event. The apparatus may also stop recording data upon receipt of an indication that a data transfer should be initiated. Exemplary indications include a wireless data transfer request, removal of the memory card, or a connection to the data interface, depending on the data transfer configuration of the apparatus.

If a wireless neural activity recording apparatus is used, at transfer data 1116 data is transferred wirelessly. Data may be wirelessly transferred upon receipt of a transfer request. Exemplary transfer requests may be initiated by activation of a switch provided for that purpose or upon transmission to the apparatus of a request for transfer. If the neural activity recording apparatus is configured for single use, the apparatus may automatically inhibit further recording after a successful transfer. The apparatus may also be configured as a limited uses apparatus by programming a permitted number of uses and disabling the apparatus after the permitted number of uses has been achieved, which may be determined by the number of executed data transfers.

If a non-wireless neural activity recording apparatus is used, at tear housing 1114 the housing of the apparatus is torn to enable removal of the memory card or connection to the data interface. The data is then transferred to an external processing or recording device by inserting the memory card or initiating a data transfer though the data interface.

At dispose apparatus 1130, the apparatus is disposed after the single use or after the predetermined limited number of uses.

As used herein, the transitional term "comprising", which is synonymous with "including," or "containing," is inclusive or open-ended and does not exclude additional, unspecified elements or method steps. By contrast, the transitional term "consisting" is a closed term which does not permit addition of unspecified terms.

As used herein, an algorithm or, processing sequence, is a self consistent sequence of instructions that can be followed to perform a particular task. Computer software, or software, executes an algorithm and can be divided into application software, or application, and systems software. An application executes instructions for an end-user, or user, where systems software consists of low-level programs that operate between an application and hardware. Systems software includes operating systems, compilers, and utilities for managing computer resources. While computing systems typically include systems software and applications software, they may also operate with software that encompasses both application and systems functionality. Applications may use data structures for both inputting information and performing the particular task. Data structures greatly facilitate data management. Data structures are not the information content of a memory, rather they represent specific electronic structural elements which impart a physical organization on the information stored in memory. More than mere abstraction, the data structures are specific electrical or magnetic structural elements in memory which simultaneously represent complex data accurately and provide increased efficiency in computer operation.

As used herein, a processing device may be a specifically constructed apparatus or may comprise general purpose computers selectively activated or reconfigured by software stored therein. The processing device, whether specifically constructed or general purpose, has at least one processor, or processing device, for executing machine instructions, which may be grouped in processing sequences, and access to memory for storing instructions and other information. Many combinations of processing circuitry and information storing equipment are known by those of ordinary skill in these arts. A processor may be a microprocessor, a digital signal processor (DSP), a central processing unit (CPU), or other circuit or equivalent capable of interpreting instructions or performing logical actions on information. Memory includes both volatile and non-volatile memory, including temporary and cache, in electronic, magnetic, optical, printed, or other format used to store information. Exemplary computing devices include workstations, personal computers, portable computers, portable wireless devices, mobile devices, and any device including a processor, memory and software. Computing systems encompass one or more computing devices and include computer networks and distributed computing devices.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A neural activity recording apparatus comprising:
at least two electrodes configured to establish an electrical path through a patient's skin and to acquire a neural activity signal;
an amplifier circuit configured to output an amplified neural activity signal based on the neural activity signal;
an integrated circuit chip (IC) including an instrumentation amplifier to receive and amplify the amplified neural activity signal from the amplifier circuit, a processor, an analog-to-digital converter (ADC), an on-board memory, and a line frequency filter algorithm embedded in the on-board memory, the ADC configured to digitize an amplified neural activity signal from the instrumentation amplifier to produce a sample stream, and the line frequency filter algorithm configured to cancel a substantial portion of a line frequency signal embedded in the sample stream to generate a neural activity data;
a removable memory configured to store the neural activity data;
an energy storage device configured to energize the IC; and
a housing sealingly enclosing the IC, the amplifier circuit, the removable memory and the energy storage device, the housing configured to be unsealed to enable removal of the removable memory,
wherein the neural activity recording apparatus is sized to be attached to and supported by the patient's forehead and energized solely by the energy storage device, and
wherein the activity recording apparatus is devoid of an isolation circuit, wherein the IC is directly electrically coupled to the patient's skin and to the energy storage device and to the removable memory, without an external connection to power the activity recording apparatus and store the neural activity data, wherein the neural activity data is configured to diagnose sleep/wake patterns during a time period limited by the energy stored in the energy storage device.

2. A neural activity recording apparatus as in claim 1, wherein the IC includes two or more amplifier circuits, and the instrumentation amplifier circuit is configured with the two or more amplifier circuits.

3. A neural activity recording apparatus as in claim 1, wherein the amplifier circuit is positioned near one of the at least two electrodes.

4. A neural activity recording apparatus comprising:
at least two electrodes configured to establish an electrical path through a patient's skin and to acquire a neural activity signal;
an amplifier circuit configured to output an amplified neural activity signal based on the neural activity signal;
an integrated circuit chip (IC) including an instrumentation amplifier to receive and amplify the amplified neural activity signal from the amplifier circuit, a processor, an analog-to-digital converter (ADC), an on-board memory, and a line frequency filter algorithm embedded in the on-board memory, the ADC configured to digitize an amplified neural activity signal from the instrumentation amplifier to produce a sample stream, and the line frequency filter algorithm configured to cancel a substantial portion of a line frequency signal embedded in the sample stream to generate a neural activity data;
a removable memory configured to store the neural activity data;
an energy storage device configured to energize the IC; and
a housing sealingly enclosing the IC, the amplifier circuit, the removable memory and the energy storage device, the housing configured to be unsealed to enable removal of the removable memory,
wherein the neural activity recording apparatus is sized to be attached to and supported by the patient's forehead and energized solely by the energy storage device, and
wherein the ADC samples the amplified neural activity signal at an integer multiple of a power line frequency, the multiple being greater than 2, and wherein to cancel a substantial portion of a line frequency signal embedded in the sample stream the line frequency filter algorithm is configured to divide the sample stream into a number of sub-streams corresponding to the line frequency multiple, to compute moving averages for each sub-stream, and to subtract the moving averages from each sub-stream to cancel the residual line noise from each sub-stream.

5. A neural activity recording apparatus as in claim 1, wherein the IC further includes an analog-to-digital converter (ADC) configured to generate and provide a common mode feedback signal to the instrumentation amplifier to substantially cancel a common mode signal in the neural activity signal.

6. A neural activity recording apparatus as in claim 1, further comprising an indicator device configured to provide a sleep quality feedback, wherein the indicator device is integrated with the neural activity recording apparatus, and wherein the IC comprises an algorithm configured to determine the sleep quality feedback and to provide an indication thereof with the indicator device.

7. A neural activity recording apparatus as in claim 6, where the indicator device is configured to continuously provide the sleep quality feedback.

8. A neural activity recording apparatus as in claim 6, further comprising a transducer outputting transducer signals, wherein the transducer is integrated with the neural activity recording apparatus, and wherein the IC correlates the transducer signals with the neural activity data to determine the sleep quality feedback.

9. A neural activity recording apparatus as in claim 8, wherein the transducer comprises at least one of a motion transducer and an air flow transducer.

10. A neural activity recording apparatus as in claim 1, further comprising an adhesive material on one side of the housing, the adhesive material configured to adhere the housing to the patient's skin, wherein the activity recording apparatus is sized and configured to be entirely supported by the adhesive material adhered to the patient's skin.

11. A method of recording neural activity with a neural activity recording apparatus, the method comprising:
attaching the neural activity recording apparatus to the patient, the neural activity recording apparatus including at least two electrodes configured to establish an electrical path through a patient's skin and to acquire a neural activity signal; an amplifier circuit configured to output an amplified neural activity signal based on the neural activity signal; an integrated circuit chip (IC) including a processor, an instrumentation amplifier to receive and amplify the amplified neural activity signal from the amplifier circuit, an analog-to-digital converter (ADC), an on-board memory, and a line frequency filter algorithm embedded in the on-board memory, and the ADC configured to digitize an amplified neural activity signal from the instrumentation amplifier to produce a sample stream; a removable memory configured to store the neural activity data; an energy storage device configured to energize the IC; and a housing sealingly enclosing the IC, the instrumentation amplifier, the removable memory and the energy storage device, the housing configured to be unsealed to enable removal of the removable memory, wherein the neural activity recording apparatus is sized to be attached to and supported by the patient's forehead and energized solely by the energy storage device, wherein the activity recording apparatus is devoid of an isolation circuit, wherein the IC is directly electrically coupled to the patient's skin and to the energy storage device and to the removable memory, without an external connection to power the activity recording apparatus and store the neural activity data, and wherein the neural activity data is configured to diagnose sleep/wake patterns during a time period limited by the energy stored in the energy storage device;

powering the neural activity recording apparatus with the energy storage device;

amplifying the amplified neural activity signal from the amplifier circuit to generate an amplified neural activity signal by the instrumentation amplifier;

generating a sample stream from the amplified neural activity signal from the instrumentation amplifier circuit;

canceling, with the line frequency filter algorithm, a substantial portion of a line frequency noise signal embedded in the sample stream to generate a neural activity data substantially free of the line frequency noise signal;

storing the neural activity data in a removable memory;

unsealing the housing to enable removal of the removable memory; and removing the removable memory.

12. A neural activity recording method as in claim 11, wherein unsealing comprises permanently damaging the housing.

13. A neural activity recording method as in claim 11, further comprising discarding the neural activity recording apparatus after a single use.

14. A neural activity recording method as in claim 11, further comprising sampling the amplified neural activity signal at an integer multiple of a power line frequency, the multiple being greater than 0.

15. A neural activity recording method as in claim 14, further comprising dividing the sample stream into at least two sub-streams, computing moving averages for each sub-stream, and computing the neural activity data based on the moving averages of the at least two sub-streams.

16. A neural activity recording method as in claim 11, further comprising providing a common mode feedback signal to the instrumentation amplifier to cancel a common mode signal embedded in the neural activity signal.

17. A neural activity recording method as in claim 16, further comprising an indicator device configured to provide a sleep quality feedback.

18. A neural activity recording apparatus as in claim 1, wherein configured to be unsealed comprises configured to be permanently damaged in order to remove the removable memory.

19. A neural activity recording apparatus as in claim 1, further comprising a conductor connecting the IC to the amplifier circuit to provide a common-mode reference signal thereto.

20. A neural activity recording apparatus as in claim 1, wherein the amplifier circuit is positioned in the housing near one of the at least two electrodes and the IC is positioned in the housing near another of the at least two electrodes to reduce noise.

21. A neural activity recording apparatus as in claim 1, wherein the neural activity recording apparatus comprises physiologically relevant signature patterns and is configured to compare the physiologically relevant signature patterns to the neural activity data to identify physiologically relevant data, and wherein the neural activity recording apparatus is configured to only store in the removable memory the physiologically relevant data.

22. A neural activity recording apparatus as in claim 1, wherein the ADC samples the amplified neural activity signal at an integer multiple of a power line frequency, the multiple being greater than 2, and wherein to cancel a substantial portion of a line frequency signal embedded in the sample stream the line frequency filter algorithm is configured to divide the sample stream into a number of sub-streams corresponding to the line frequency multiple, to compute moving averages for each sub-stream, and to subtract the moving averages from each sub-stream to cancel the residual line noise from each sub-stream.

* * * * *